(12) United States Patent
Fareed

(10) Patent No.: US 7,004,920 B2
(45) Date of Patent: Feb. 28, 2006

(54) ANKLE TREATING APPARATUS AND METHOD OF USING SAME

(76) Inventor: Donald O. Fareed, P.O. Box 50509, Montecito, CA (US) 91350-0509

( * ) Notice: Subject to any disclaimer, the term of this patent is extended or adjusted under 35 U.S.C. 154(b) by 0 days.

(21) Appl. No.: 10/843,598

(22) Filed: May 10, 2004

(65) Prior Publication Data

US 2005/0251085 A1 Nov. 10, 2005

(51) Int. Cl.
*A61F 13/00* (2006.01)
(52) U.S. Cl. .............................. 602/65; 602/60; 602/61
(58) Field of Classification Search ................. 602/26, 602/27, 60–62, 65, 64; 128/877, 892; D24/192; 2/22
See application file for complete search history.

(56) References Cited

U.S. PATENT DOCUMENTS

| 3,527,211 | A |   | 9/1970 | Baker |
| 4,409,976 | A |   | 10/1983 | Pence |
| 5,520,628 | A |   | 5/1996 | Wehr |
| 5,769,810 | A |   | 6/1998 | Brossard |
| 5,796,316 | A | * | 8/1998 | Romerein ................... 333/100 |
| 6,503,218 | B1 |   | 1/2003 | Ascheman |

* cited by examiner

*Primary Examiner*—Kim M. Lewis
(74) *Attorney, Agent, or Firm*—James E. Brunton, Esq.

(57) ABSTRACT

A method and apparatus for treating ankle pain, ankle sprains and ankle swelling. The apparatus includes the strategically located pressure imparting pads which are applied over the ankle of the user in a manner to provide focused anterior pain relieving pressure to the ankle. The apparatus when in place about the users ankle, permits substantially full ankle function.

9 Claims, 5 Drawing Sheets

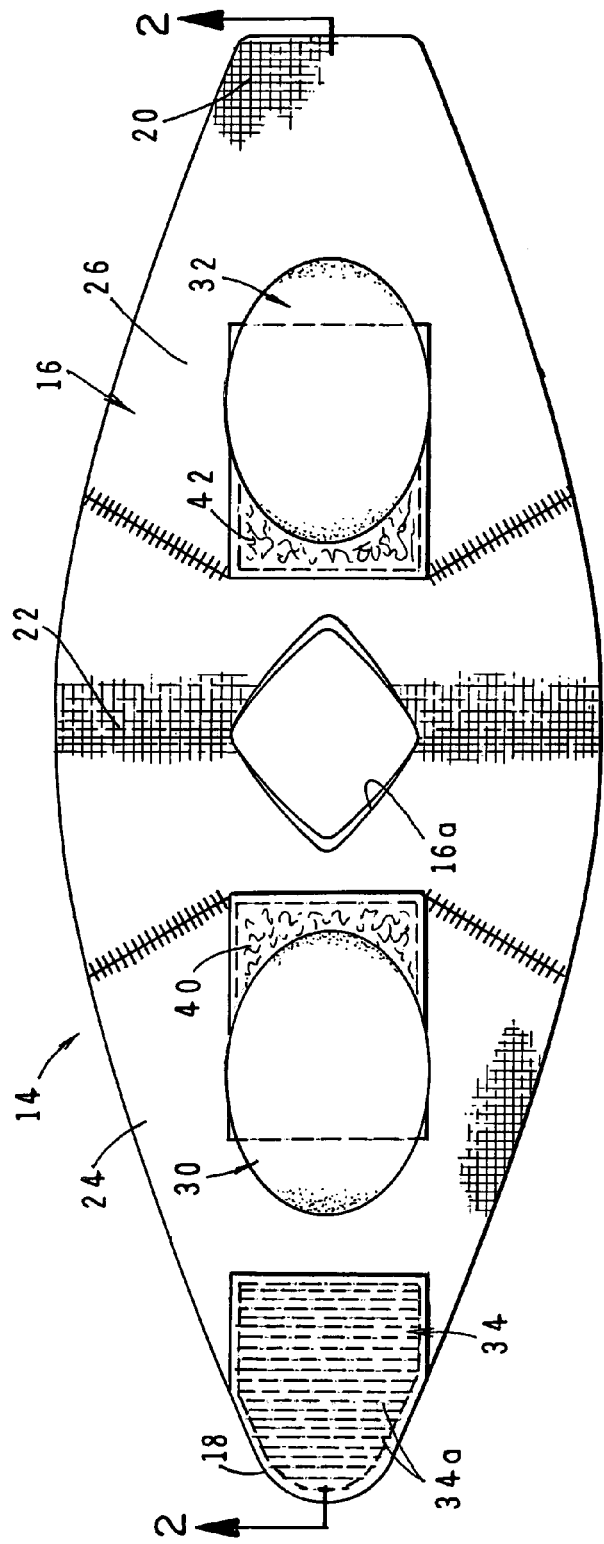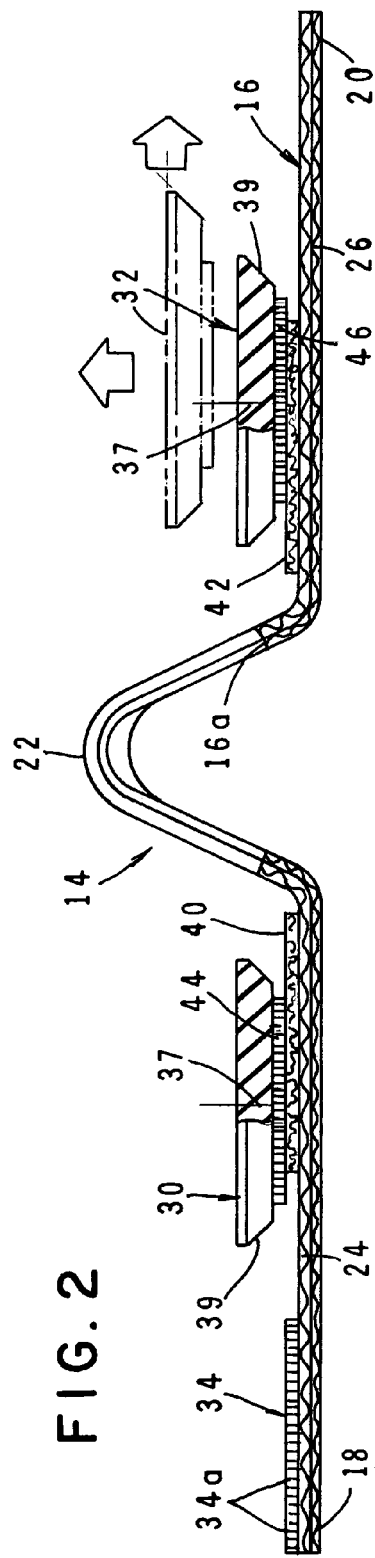

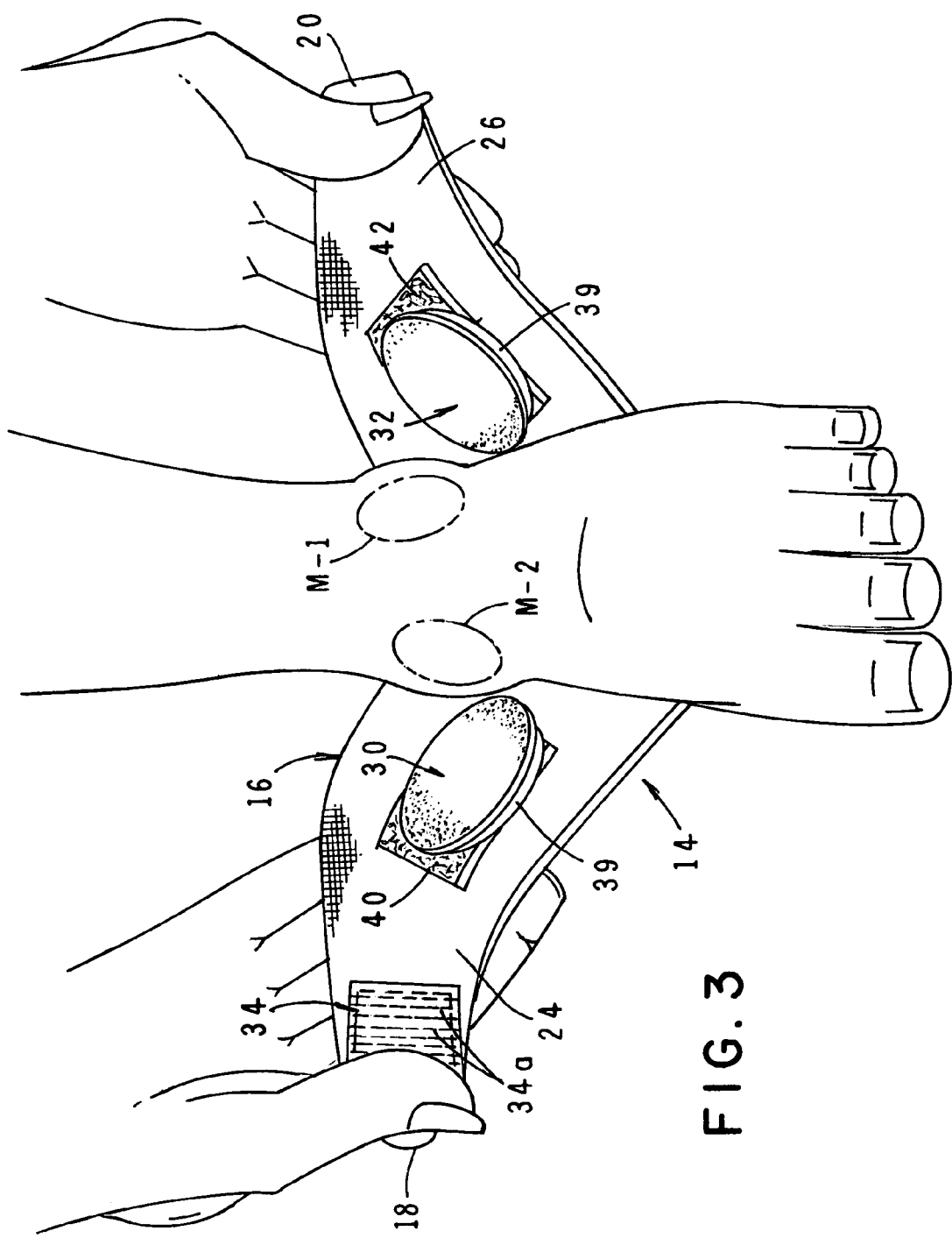

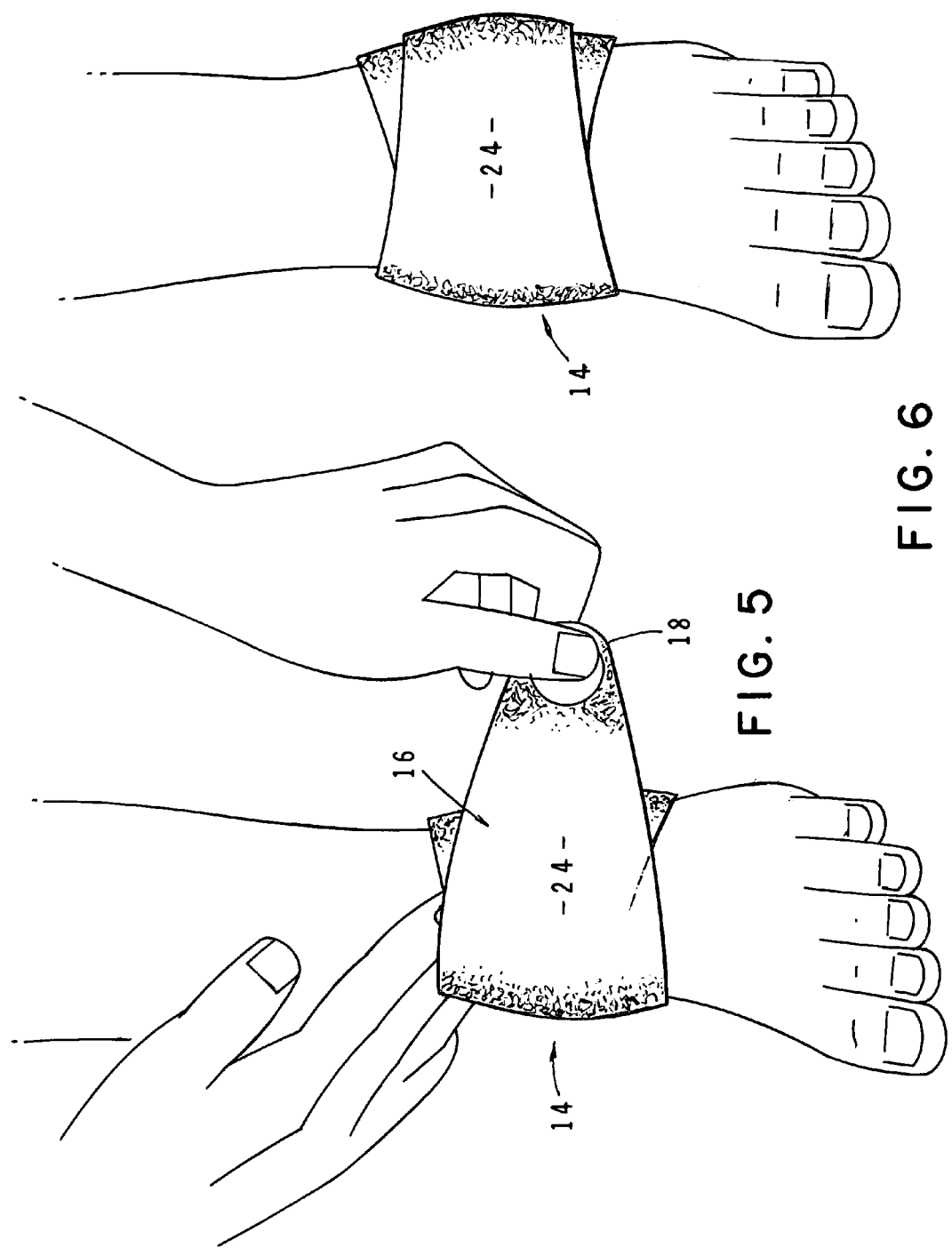

ANKLE TREATING APPARATUS AND METHOD OF USING SAME

BACKGROUND OF THE INVENTION

1. Field of the Invention

The present invention relates generally to a method and apparatus for treating ankle pain, ankle sprains and ankle swelling. More particularly, the invention concerns a method in which two strategically located pads are applied over the front of the ankle of the patient and a focused, anterior compression is applied to the pads to provide immediate relief of ankle pain.

2. Discussion of Prior Art

The prior art is replete with various types of methods and apparatus to support the ankle, both to prevent ankle sprains and to protect the ankle during rehabilitation from ankle sprains and other ankle injuries. A commonly used prior art technique for guarding against ankle sprain and for preventing reinjury of a sprained ankle is to tape the ankle joint in a manner to partially restrict movement of the ankle. Another common prior art technique for protecting the ankle against injury is to provide some type of structural ankle brace that is positioned over the ankle in a manner to support the ankle.

Exemplary of a prior art structural type ankle brace is that disclosed in U.S. Pat. No. 6,503,218 B1 issued to Ascherman. This device comprises an in-the-shoe ankle brace that includes an anklebone cover and an adjustable fastening means for removably affixing the brace to the ankle. Another type of ankle brace, or ankle support, is disclosed in U.S. Pat. No. 3,527,211 issued to Baker. The Baker ankle support is constructed from two similar pieces of elastic material and includes joints at the ankle region. The Baker support also includes an arch member and an encircling member that encircles the Achilles tendon. Elastic fastening means are provided for tightening the support around the ankle.

Still another type of ankle support is disclosed in U.S. Pat. No. 4,409,976 issued to Pence. This latter ankle support has a main body portion adapted to extend about the Achilles tendon of the foot along the inner and outer sides of the foot with the tongue portion and overlapping first strap portion passing across the ankle to completely encircle the ankle of the user. The Pence apparatus also includes a stirrup portion that depends from the body portion so as to pass beneath the arch and sole of the foot leaving the heel exposed.

U.S. Pat. No. 5,520,628 issued to Wehr discloses an ankle encompassing pressure orthosis that is provided in the form of a custom fitted ankle brace comprised of anterior and posterior supports that are connected together at their distal ends by pivot pins. An announced primary object of the Wehr invention is to provide a custom fitted brace, which limits inversion and eversion of the ankle and foot while allowing unhindered dorsiflexion and plantar flexion of the ankle and foot.

U.S. Pat. No. 5,769,810 issued to Brossard discloses a method for controlling the reflex response of the muscles of the ankle joint. An announced object of the Brossard invention is to use a specific mechanical stimulation at an articulated body joint to increase the reflex response and therefore the efficiency of the muscles associated to the joint and hence to prevent the joint muscles from becoming oversolicited and therefore to prevent the joint muscles from suffering from repetitive motion syndromes.

As will be better understood from the discussion which follows, unlike the prior art methods and apparatus, the method and apparatus of the present invention is directed specifically to treating ankle pain, ankle sprains and ankle swelling by applying focused anterior compression on the anterior/lateral margins of the ankle. Further, the apparatus of the present invention differs from the typical prior art ankle wraps and supports, which typically provide circumferential compression to the ankle. More particularly, unlike the prior art circumferential wraps and supports, the compressive forces exerted by the apparatus of the present invention are uniquely focused to selected specific locations at the front of the ankle, along the margins of the ankle, and proximate the anterior ankle mortise. In sharp contradiction to the prior art support devices which provide circumferential support but do not localize compression to the anterior ankle mortise, the apparatus of the present invention provides a uniquely focused pain relieving compressive forces to the anterior ankle. Similarly, the apparatus of the present invention differs substantially from prior art structural type ankle braces, such as those previously described herein, which are applied medially and laterally with splinting in a stirrup fashion. Uniquely, the apparatus of the present invention allows for full ankle function, without immobilizing the ankle during the time of treatment. In one form of the present invention, the ankle treating apparatus includes a pair of generally oval shaped compressive pads which are applied directly over the anterior/medial and anterior/lateral ankle mortise. These compressive pads are preferably between about 1.5 inches and about 2.5 inches in width and between about 2.5 inches to 3.5 inches in length.

Compression is applied to both of these pads at an angle of between about 30° and about 45° by means of a uniquely configured split strap measuring about 15 inches in length and about 6 inches in width with a centered heel receiving opening for the receiving heel users.

In use, the two compressor pads are applied over the front of the ankle, with an anterior axis being between about 110 degrees and about 150 degrees. The focused anterior compression provided by the strategically positioned compression pads allows for immediate relief of pain which emanates from the anterior/medial and anterior/lateral margins of the ankle.

BRIEF DESCRIPTION OF DRAWINGS

FIG. 1 is a top plan view of one form of the apparatus of the invention.

FIG. 2 is a cross sectional view taken along lines 2—2 of FIG. 1.

FIG. 3 is a generally diagrammatic view illustrating the initial step in positioning the apparatus about the patient's ankle.

FIG. 5 is a generally diagrammatic view, similar to FIG. 4 further illustrating the positioning of the device about the patient's ankle.

FIG. 6 is front view of the apparatus as it appears in position about the patient's ankle.

SUMMARY OF THE INVENTION

Figure 3A:
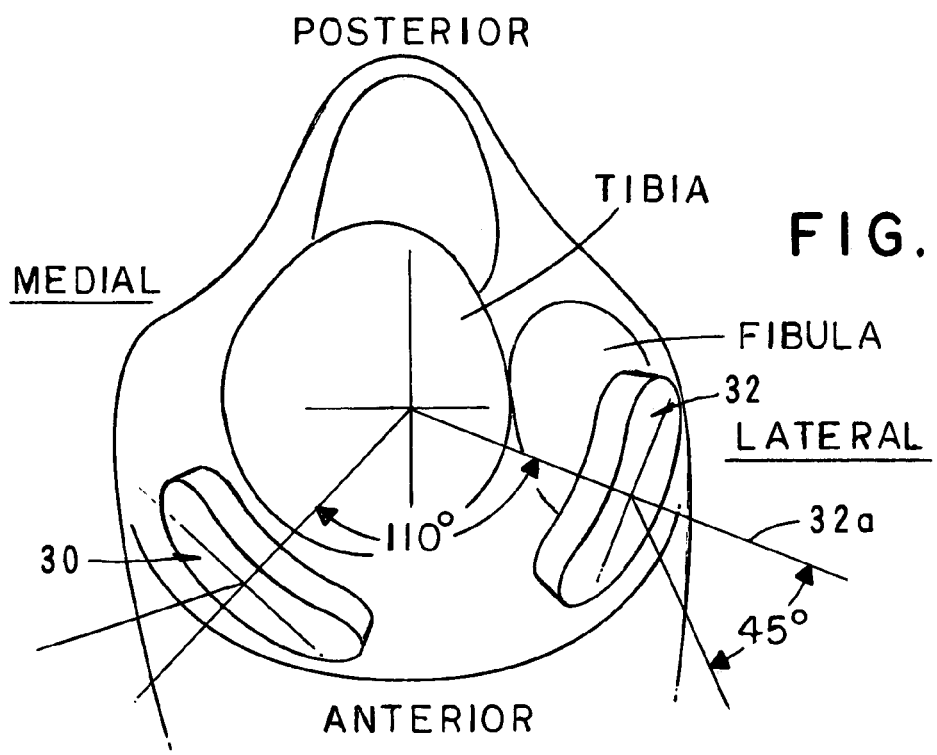
FIG. 3A is a generally diagrammatic view illustrating a first relative positioning of the pressure imparting pads of the device.

By way of brief summary, one form of the apparatus of the present invention for attachment to the ankle of the user for treating ankle pain, ankle sprains and ankle swelling of the user comprises an elongated strap having first and second ends and an apertured central portion for receiving the heel of the user. Adjustably connected to the strap between the first end and the apertured central portion thereof strap is a first generally oval shaped pressure imparting pad and adjustably to the strap connected between a second end and the apertured central portion thereof is a second generally oval shaped pressure imparting pad. Uniquely, the first and second pressure imparting pads can be adjustably connected to the strap in a manner such that the central axis of the second pad extends an angle of between about 110 degrees and about 150 degrees relative to the central axis of the first pad. With this construction, when the first and second ends of the strap are interconnected by the connector means of the invention, the compression pads will focus pain relieving pressure at strategically selected locations on the ankle of the patient.

It is an object of the present invention to provide a method and apparatus for treating ankle pain, ankle sprains and ankle swelling.

Another object of the invention is to provide an apparatus of the aforementioned character in which two strategically located pressure imparting pads are applied over the ankle of the user in a manner to provide focused anterior pain relieving pressure to the ankle.

Another object of the invention is to provide an apparatus as described in the preceding paragraph in which the apparatus, when in place about the users ankle permits substantially full ankle function.

Another object of the invention is to provide an apparatus of the character described which is readily adjustable and easy to use.

Another object of the invention is provide an apparatus as described in the preceding paragraphs that is of simple construction, is durable in use and one that can be inexpensively manufactured.

DESCRIPTION OF THE INVENTION

Referring to the drawings and particularly to FIGS. 1, 2 and 3, one form of the apparatus of the invention is there shown and generally designated by the numeral 14. In this embodiment of the invention the apparatus comprises a strap 16 having first and second ends 18 and 20 respectively and an apertured heel receiving central portion 22. As best seen in FIG. 1, a first intermediate portion 24 is located between first end 18 and said central portion 22 and a second intermediate portion 26 is located between second end 20 and central portion 22.

As indicated in FIGS. 1 and 2 first pressure imparting pad 30 is connected to strap 16 proximate the first intermediate portions 24 and a second pressure imparting pad 32 is adjustably connected to strap 16 proximate the second intermediate portion 26. In a manner presently to be described, first pressure imparting pad 30 is advantageously, adjustably movable between a first location and a second location. In a similar manner, second pressure imparting pad 32 is advantageously, adjustably movable between a third location and a fourth location.

As previously mentioned, strap 16 is preferably about 15 in. in length and about 6 in. in width with a centered, generally diamond shaped heel receiving opening 16a for receiving the heel of the user. In the present form of the invention compression pads 30 and 32 are generally oval in shape and are preferably constructed from a suitable semi-rigid elastomeric material. As illustrated in FIG. 2, each of the first and second pressure pads has a central portion 37 of a first thickness and a tapered peripheral portion 39 of a second thickness less than the first thickness. In the present form of the invention pads 30 and 32 are between about 1.5 inches and about 2.5 inches in width and about 2.5 inches to 3.5 inches in length. As previously mentioned, the position of the pads can be strategically adjusted relative to the supporting strap so that each of the pads can be applied directly over the anterior/medial and anterior/lateral ankle mortise of the user.

Connector means are provided for releasably interconnecting the first and second ends of the strap in a manner to cause the first and second pressure imparting pads to exert a precisely focused pressure on the ankle of the user. This focused anterior compression provided by the strategically positioned compression pads allows for immediate relief of pain, which emanates from the anterior/medial and anterior/lateral margins of the ankle. The connector means of the invention here comprise a connector patch 34 that as connected proximate first end 18 of strap 16 in the manner shown in FIGS. 1 and 2.

Connector patch 34 is here provided with a multiplicity of small hooks 34a that are so constructed and arranged to releasably grip the surface of the fabric located proximate the second end of the strap in the manner shown in FIG. 6. While connector patch 34 can take several forms it is preferably constructed from a material sold under the name and style VELCRO.

In order to permit adjustment of pads 30 and 32 relative to strap 16, first and second pad connector means, or pad connector patches 40 and 42 are affixed to strap 16 intermediate its ends in the manner best seen in FIG. 1. While these connector patches can take several forms they are also preferably constructed from a material sold under the name and style VELCRO.

Figure 3B:
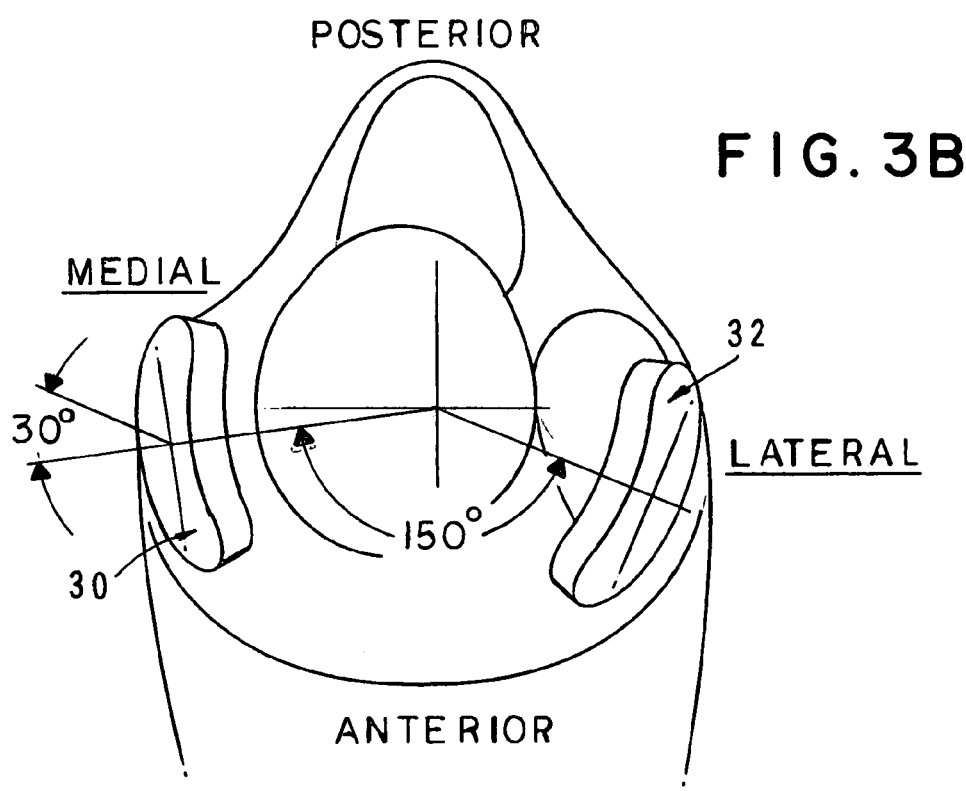
FIG. 3B is a generally diagrammatic view similar to FIG. 3A, illustrating a second relative positioning of the pressure imparting pads of the device.
Figure 4:
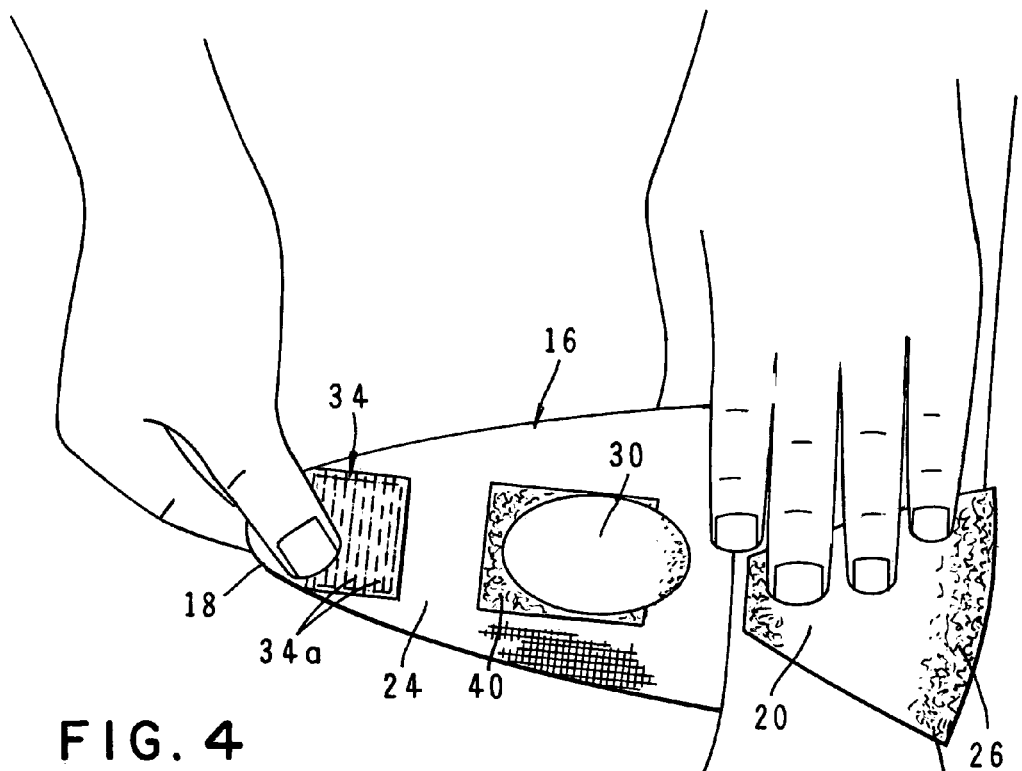
FIG. 4 is a generally diagrammatic view similar to FIG. 3, but showing a further step in positioning the device about the ankle of the patient.

As illustrated in FIG. 2, similar connector patches 44 and 46 are connected to pads 30 and 32 respectively. Connector patches 44 and 46 are here provided with a multiplicity of small hooks which are adapted to be received within a multiplicity of small loops provided on pad connector patches 40 and 42. With the construction thus described, each of the patches 30 and 32 can be readily disconnected from connector patches 40 and 42 and repositioned relative thereto in the manner illustrated in FIGS. 3A and 3B. More particularly, as shown in these figure drawings, the first and second pressure imparting pads can be adjustably connected to the strap in a manner such that the central axis 32a of said second pad 32 extends at an angle of between about 110 degrees and about 150 degrees relative to the central axis 30a of first pad 30. As also shown by FIGS. 3A and 3B, when the device is positioned about the user's ankle in the manner shown in FIG. 6, strategically focused compression is applied to both of the pads at an angle of between about 30° and about 45°.

Figure 7:
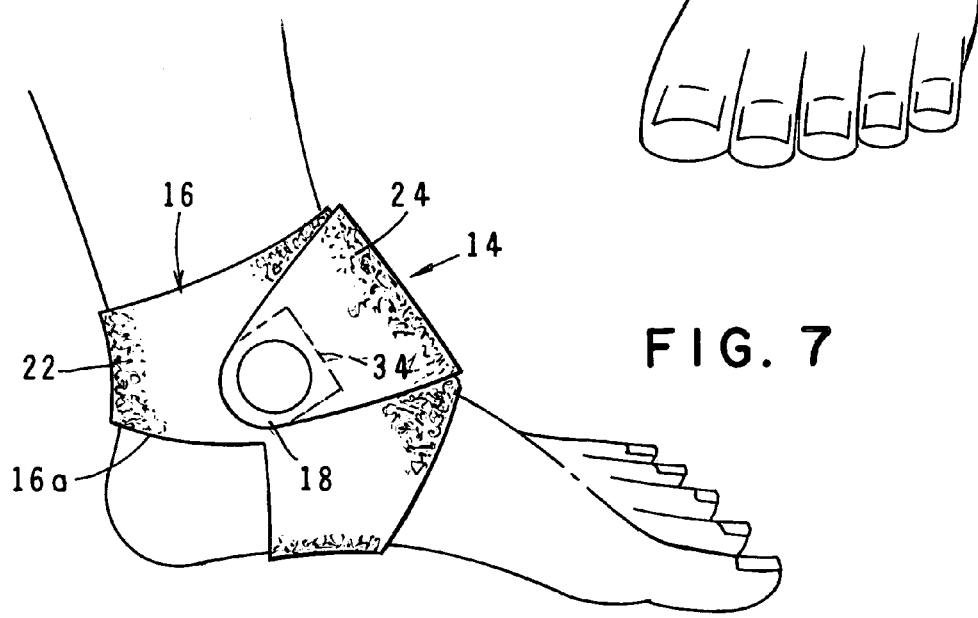
FIG. 7 is a side view of the apparatus as it appears in position about the patient's ankle.

In using the apparatus of the invention, with the pads 30 and 32 positioned relative to the strap 16 so that they can be applied directly over the user's anterior/medial and anterior/lateral ankle mortise, the strap 16 is next positioned about the foot of the user in the manner shown in FIG. 3 of the drawings. In this position, the heel of the user is disposed within the generally diamond-shaped opening 16a (FIGS. 1 and 7). This done, the second end 20 of the strap 16 is wrapped about the user's ankle in the manner shown in FIG.

4 so that the compression pad 32 is strategically positioned over the ankle mortise M-1. Next, the first end 18 of the strap is wrapped about the user's ankle in the manner shown in FIG. 5 so as to bring the compression pad 30 into position over the mortise M-2 (FIG. 3). With the compression pad 30 in engagement with the mortise M-2, the connector patch 34 is brought into engagement with the strap 16 in the manner shown in FIGS. 6 and 7 so as to securely affix the apparatus to the ankle of the user with the device thereby secured about the user's ankle the strategically positioned compression pads effectively focus pain relieving pressure to the users ankle thereby alleviating the pain and reducing ankle swelling.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

I claim:

1. An apparatus for attachment to the ankle of a user for treating ankle pain, ankle sprains and ankle swelling of the user comprising:
    (a) a strap having first and second ends, a central portion, a first intermediate portion located between said first end and said central portion and a second intermediate portion located between said second end and said central portion;
    (b) a first pressure imparting pad having an exterior surface and a central axis, said first pressure imparting pad being adjustably connected to said strap proximate said first intermediate portion for movement between a first location and a second location, said central axis of said strap extending at an angle of between about 110 degrees and about 150 degrees relative to said central axis of said first pad;
    (c) a second pressure imparting pad having an exterior surface and a central axis said second pressure imparting pad being adjustably connected to said strap proximate said second intermediate portion for movement between a third location and a fourth location, said central axis of said strap extending at an angle of between about 110 degrees and about 150 degrees relative to said central axis of said second pad; and
    (d) connector means for releasably interconnecting said first and second ends of said strap in a manner to impart pressure to said pressure imparting pads at an angle of between about 30 degrees and about 45 degrees relative to said exterior surface of said pads to cause said first and second pressure imparting pads to exert focused pressure on the anterior ankle of the user.

2. The apparatus as defined in claim 1 in which said first and second pressure imparting pads are oval in shape.

3. The apparatus as defined in claim 1 in which said first and second pressure imparting pads have a central portion of a first thickness and a peripheral portion of a second thickness less than said first thickness.

4. The apparatus as defined in claim 1 in which said central portion of said strap is apertured to provide a heel receiving opening.

5. An apparatus for attachment to the ankle of a user for treating ankle pain, ankle sprains and ankle swelling of the user comprising:
    (a) a strap having first and second ends, a central portion, a first intermediate portion located between said first end and said central portion and a second intermediate portion located between said second end and said central portion;
    (b) a first generally oval-shaped pressure imparting pad having an exterior surface, a central axis, a central portion of a first thickness and a peripheral portion of a second thickness less than said first thickness said padding being adjustably connected to said strap proximate said first intermediate portion, said first pressure imparting pad having a central axis;
    (c) a second generally oval-shaped pressure imparting pad having an exterior surface, a central axis, a central portion of a first thickness and a peripheral portion of a second thickness less than said first thickness and being adjustably connected to said strap proximate said second intermediate portion in a manner such that the central axis of said second pad extends at an angle, of between about 110 degrees and about 150 degrees relative to the central axis of said first pad; and
    (d) connector means for releasably interconnecting said first and second ends of said strap in a manner to impart pressure to said pressure imparting pads at an angle of between about 30 degrees and about 45 degrees relative to said exterior surface of said pads to cause said first and second pressure imparting pads to exert pressure on the anterior ankle of the user when said first and second pressure imparting pads are affixed to said strap.

6. The apparatus as defined in claim 5 in which said central portion of said strap is apertured to provide a heel receiving opening.

7. An apparatus for attachment to the ankle of a user for treating ankle pain, ankle sprains and ankle swelling of the user comprising:
    (a) a strap having first and second ends, an apertured central portion, a first intermediate portion located between said first end and said central portion and a second intermediate portion located between said second end and said central portion;
    (b) a first generally oval-shaped pressure imparting pad adjustably connected to said strap proximate said first intermediate portion, said first pressure imparting pad having a central axis and a central portion of a first thickness and a peripheral portion of a second thickness less than said first thickness;
    (c) a second generally oval-shaped pressure imparting pad having a central axis and a central portion of a first thickness and a peripheral portion of a second thickness less than said first thickness and being adjustably connected to said strap proximate said second intermediate portion in a manner such that the central axis of said second pad extends an angle, of between about 110 degrees and about 150 degrees relative to the central axis of said first pad; and
    (d) connector means for releasably interconnecting said first and second ends of said strap in a manner to cause said first and second pressure imparting pads to exert pressure on the ankle of the user at an angle of between about 30° and about 45° when said first and second pressure imparting pads are affixed to said strap.

8. The apparatus as defined in claim 7 in which said first and second pressure imparting pads have a central portion of a first thickness and a peripheral portion of a second thickness less than said first thickness.

9. The apparatus as defined in claim 7 in which said connector means comprises a connector connected proximate said first end of said strap, said connector having a multiplicity of hooks for grippingly engaging said strap.

* * * * *